United States Patent [19]

Ditter et al.

[11] 4,065,509

[45] Dec. 27, 1977

[54] SYNTHESIS OF β-METHYL DERIVATIVES OF 2,4-DICARBA-CLOSO-HEPTABORANE-7

[75] Inventors: Jerome F. Ditter, Santa Ana; Eugene B. Klusmann, Irvine, both of Calif.

[73] Assignee: The United States of America as represented by the Secretary of the Navy, Washington, D.C.

[21] Appl. No.: 689,893

[22] Filed: May 25, 1976

[51] Int. Cl.$^2$ .............................................. C07F 5/02
[52] U.S. Cl. ............................................ 260/606.5 B
[58] Field of Search ................................. 260/606.5 B

[56] References Cited
PUBLICATIONS

Dunks et al., Inorg. Chem., vol. 9, pp. 893 to 898 (1970).

Grafstein et al., Inorg. Chem., vol. 2, pp. 1120 to 1125 (1963).

Dunks et al., Inorg. Chem., vol. 8, pp. 2667 to 2671 (1969).

Primary Examiner—Helen M. S. Sneed
Attorney, Agent, or Firm—R. S. Sciascia; Philip Schneider; Thomas McDonnell

[57] ABSTRACT

The β-methylation of 2,4-dicarba-closo-heptaborane-7 through the reaction of methyl chloride with the parent carborane in the presence of metal trichloride selected from the group consisting of aluminum chloride and ferric chloride in a methyl chloride-to-carborane mole ratio from 1:1 to 6:1 and a metal trichloride-to-carborane from 0.3:1 to 5:1 at a temperature from about 30° C to about 60° C and at a pressure of at least 50 psig.

6 Claims, No Drawings

SYNTHESIS OF β-METHYL DERIVATIVES OF 2,4-DICARBA-CLOSO-HEPTABORANE-7

BACKGROUND OF THE INVENTION

The present invention pertains to boro-organic synthesis and more particularly to the methylation of boron atoms in carboranes.

The substitution of methyl groups on the boron atoms of carboranes is advantageous in that polymers derived from B-methylated carboranes often have improved properties. For example the B-methyl derivatives of 2,4-dicarba-closo-heptaborane-7 exhibit high thermal stability and thus would provide excellent high temperature elastomers.

The only method presently being used for methylating carboranes involves pyrolysis of a nido-carborane in the presence of excess trimethylborane. This method is unsatisfactory on account of the low yields. Various B-methylated derivatives have been produced as a by-product in the reaction of pentaborane-9 with acetylene in a flow system, but the yields are extremely small — trace amounts only. Attempts to methylate carboranes by sequentially reacting the carborane with bromine and lithium methyl proved to be completely unsuccessful. The anticipated reaction was the removal of the bromine by formation of lithium bromide salt followed by attachment of the methyl group to the vacated boron atom. Instead, however, the bromine atom remained attached to the boron and the lithium atom substituted on the carbon atom.

SUMMARY OF THE INVENTION

It it therefore an object of this invention to provide a method for methylating the boron atoms of 2,4-dicarba-closo-heptaborane-7.

Another object of this invention is to provide a method of quickly B-methylating 2,4-dicarba-closo-heptaborane-7 in high yields and at a low cost.

These and other objects are achieved by the reaction of dicarba-closo-heptaborane-7 with methyl chloride in the presence of a substantial amount of aluminum chloride or ferric chloride under pressure and at temperatures from about 30° to 60° C whereby methyl groups are substituted on the boron atoms in relation to the amount of methyl chloride present in the reaction mixture.

DETAILED DESCRIPTION OF THE INVENTION

The process of the invention obtains a methylation of the boron atoms in preference to and in exclusion of the carbon atoms. In view of this result, the more probable mechanism of the reaction involves an attack of the skeletal boron atoms by carbonium ions formed as intermediates by the reaction of methyl chloride with aluminum chloride or ferric chloride.

The synthesis proceeds generally under a pressure of initially about 150 psig which is the vapor pressure of methyl chloride. If the reactor includes a refluxing apparatus, the pressure could be as low as 50 psig. As the reaction proceeds, the pressure increases due to by-product formation and may reach 1500 psig or higher. The temperature is maintained from about 30° to about 60° C with 47° to 53° C preferred. Depending on the reaction conditions selected, the reaction is completed within one to four days. The end point of the reaction is determined by monitoring one of the reactants, preferably the parent carborane.

In methylating 2,4-dicarba-closo-heptaborane-7 the five derivatives produced are the mono, di, tri, tetra, and penta methyl derivatives. All five derivatives are produced regardless of the amount of methyl chloride used, but one derivative predominates depending on the amount of methyl chloride present. If the mole ratio of methyl chloride to 2,4-dicarba-closo-heptaborane-7 is less than 2:1, the monomethyl derivative predominates. If the mole ratio is 5:1 or higher the pentamethyl form is the most prevalent. The intermediate mole ratios produce the corresponding derivatives. In all instances the mole ratio of aluminum chloride or ferric chloride to 2,4-dicarba-closo-heptaborane-7 is from about 0.3:1 to about 5:1 and preferably from 1:1 to 3:1. Methylation occurs preferentially at the 5-and 6- positions, which are chemically identical, followed by the 1-and 7-positions, and finally at the 3-position. This order of methylation was determined by nmr analysis of the products.

The following examples are given by way of illustration and are not intended to limit the specification or the claims to follow.

EXAMPLE I mole ratio of $CH_3Cl:2,4-C_2B_5H_7 = 2.4:1$
mole ratio of $CH_3Cl:AlCl_3 = 1.7:1$
T = 50° C
initial P = 150 psig Two closeable 1600 ml stainless steel vessels were changed with 30g (0.35 mole) of $2,4-C_2B_5H_7$, 43g (0.83) of methyl chloride, and 80g (0.60 mole) of aluminum chloride. The vessels were then heated to 50° C at which point the pressure is about 150 psig, due primarily to the vapor pressure of methyl chloride. The temperature was maintained for four days, after which time only trace quantities of unreacted $C_2B_5H_7$ was detected in the reaction products. Over this period of time the pressure in the vessel increased to 1500 psig due to the formation of hydrogen chloride and methane. The contents of both vessels were then combined, fractionally distilled, and analyzed by nmr. The results are given in Table I.

TABLE I

Results of fractional distillation of the reaction products of $2,4-C_2B_5H_7$ with methyl chloride in the presence of aluminum chloride

| Components | Boiling Temp. | Amount Recovered | Yield* |
|---|---|---|---|
| $CH_3C_2B_5H_6$ | 75–77° C | .091 mole (9g) | 12.9% |
| $(CH_3)_2C_2B_5H_5$ | 96–99° C | .274 mole (31g) | 38.8 |
| $(CH_3)_3C_2B_5H_4$ | 113–117° C | .063 mole (8g) | 8.9 |
| $(CH_3)_4C_2B_5H_3$ | 132–136° C | .028 mole (4g) | 4.0 |
| | | Total Yield | 64.6% |

*Based on initial $2,4-C_2B_5H_7$.

EXAMPLE II mole ratio of $CH_3Cl:2,4-C_2B_5H_7 = 5:1$ (molar ratio)
mole ratio of $AlCl_3:2,-4C_2B_5H_7 = 0.55:1$
T = 50° C;
$P_{init}$ = 150 psig Analysis of the product indicated that the B-pentamethyl derivative, $C_2B_5H_2(CH_3)_5$ predominated.

EXAMPLE III

Further methylation of the dimethylated carborane
mole ratio of $CH_3Cl:(CH_3)_2C_2B_5H_5 = 4.1:1$ (molar ratio)
mole ratio of $AlCl_3:(CH_3)_2C_2B_5H_5 = 3.1:1$ T = 50° C;
P$_{init}$ = 150 psig The product was the B-pentamethyl derivative obtained in 58% yield based on the initial amount of B-dimethyl carborane in the reactor Obviously many modifications and variations of the present invention are possible in light of the above teachings. It is therefore to be understood that within the scope of the appended claims the invention may be practiced otherwise than as specifically described.

What is claimed and desired to be secured by letters Patent of the United States is:

1. A method for B-methylating 2,4-dicarba-closo-heptaborane which comprises:
    admixing 2,4-dicarba-closo-heptaborane with methyl chloride in the presence of a metal trichloride in a trichloride-heptaborane mole ratio from 0.3:1 to about 5:1 in a reaction vessel;
    heating said reaction mixture to a temperature from about 30° to about 60° C;
    maintaining a pressure in said reaction vessel of at least 50 psig.

2. The method of claim 1 wherein 2,4-decorba-closo-heptaborane and methyl chloride are admixed in a mole ratio of 1:1 to 6:1.

3. The method of claim 2 wherein said metal trichloride is selected from the class consisting of aluminum chloride and ferric chloride.

4. The method of claim 3 wherein said metal trichloride is aluminum chloride.

5. The method of claim 4 wherein said aluminum chloride is present in a trichloride-heptaborane mole ratio from 1:1 to 1:3.

6. The method of claim 5 wherein said reaction temperature is from 47° to 53° C and said reaction pressure is from 150 psig to 1500 psig.

* * * * *